United States Patent [19]
Daneshvar

[11] Patent Number: 5,336,195
[45] Date of Patent: Aug. 9, 1994

[54] SPECIAL WRAPS, DILATORS AND FOLEY CATHETERS

[76] Inventor: Yousef Daneshvar, 21459 Wood Farm, Northville, Mich. 48167

[21] Appl. No.: 856,087

[22] Filed: Mar. 19, 1992

[51] Int. Cl.⁵ ............................................. A61M 5/32
[52] U.S. Cl. ................................. 604/179; 128/DIG. 26
[58] Field of Search ............. 604/174, 179, 180, 189; 128/DIG. 6, DIG. 26

[56] References Cited

U.S. PATENT DOCUMENTS

| | | | |
|---|---|---|---|
| 2,449,882 | 9/1948 | Daniels | 604/179 |
| 2,727,512 | 12/1955 | Muller | 128/DIG. 6 |
| 3,059,645 | 10/1962 | Hasbrouck et al. | 604/179 |
| 3,630,195 | 12/1971 | Santomieri | 604/180 |
| 3,698,383 | 10/1972 | Bacom | 604/189 |
| 3,905,477 | 9/1975 | Graham | 604/189 |
| 4,029,103 | 6/1977 | McConnell | 128/DIG. 26 |
| 4,096,863 | 6/1978 | Kaplan et al. | 604/129 |
| 4,316,461 | 2/1982 | Marais et al. | 128/DIG. 26 |
| 4,392,857 | 7/1983 | Beran | 128/DIG. 26 |
| 4,416,664 | 11/1983 | Womack | 604/179 |
| 4,419,094 | 12/1983 | Patel | 128/DIG. 26 |
| 4,448,894 | 5/1984 | Kovacs | 128/DIG. 26 |
| 4,453,933 | 6/1984 | Speaker | 128/DIG. 26 |
| 4,498,903 | 2/1985 | Mathew | 604/179 |
| 4,531,942 | 7/1985 | Turner | 128/DIG. 26 |
| 4,571,245 | 2/1986 | Hubbard et al. | 128/DIG. 26 |
| 4,574,798 | 3/1986 | Heitzman | 128/DIG. 26 |
| 4,583,976 | 4/1986 | Ferguson | 128/DIG. 26 |
| 4,586,919 | 5/1986 | Taheri | 604/179 |
| 4,591,356 | 5/1986 | Christie | 604/179 |
| 4,666,432 | 5/1987 | McNeish et al. | 128/DIG. 26 |
| 4,702,736 | 10/1987 | Kalt et al. | 128/DIG. 26 |
| 4,738,661 | 4/1988 | Marut | 128/DIG. 26 |
| 4,795,429 | 1/1989 | Feldstein | 128/DIG. 26 |
| 4,799,923 | 1/1989 | Campbell | 128/DIG. 26 |
| 4,846,807 | 7/1989 | Safadago | 128/DIG. 26 |
| 4,897,082 | 1/1990 | Erskine | 604/180 |
| 4,973,314 | 11/1990 | Garrett | 128/DIG. 26 |
| 4,976,698 | 12/1990 | Stokley | 128/DIG. 26 |
| 4,981,338 | 1/1991 | Taylor et al. | 128/DIG. 26 |
| 4,988,062 | 1/1991 | London | 128/DIG. 26 |
| 5,031,775 | 7/1991 | Kane | 128/DIG. 26 |
| 5,037,398 | 8/1991 | Buchanan | 128/DIG. 26 |
| 5,048,512 | 9/1991 | Turner et al. | 128/DIG. 26 |
| 5,084,026 | 1/1992 | Shapiro | 128/DIG. 26 |
| 5,116,324 | 5/1992 | Brierley et al. | 604/180 |
| 5,147,320 | 9/1992 | Reynolds et al. | 604/174 |

Primary Examiner—Paul J. Hirsch

[57] ABSTRACT

Invasive apparatus such as IV tubes, Foley catheters, arterial sheaths, Swan Ganz catheters, nasogastric tubes, or wires of temporary pacemakers are held externally on the body proximate the invasion site by a wrapping unit that has a wrap encircling a portion of the body, a support on the wrap, a cradle in the support for receiving a portion of the invasive apparatus, and either a flap, hinged cover, or rotatable latch via which the apparatus is releaseably held in the cradle. Various embodiments are disclosed, including a multi-part support in which one support part is selectively positionable on another and/or separably mounted on the latter. Various forms for the separable mounting are also disclosed. A novel form of Foley catheter is also disclosed. Also disclosed is an adaptor for adapting a conventional invasive device to one that can be received in the cradle of the support of a wrapping unit. The wrapping units are used on various portions of the body.

22 Claims, 13 Drawing Sheets

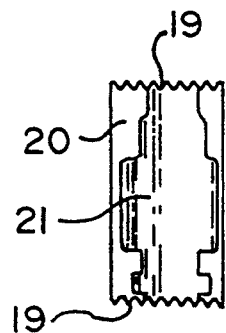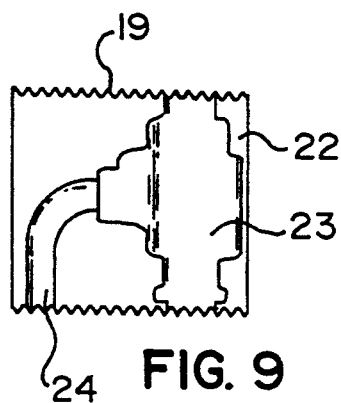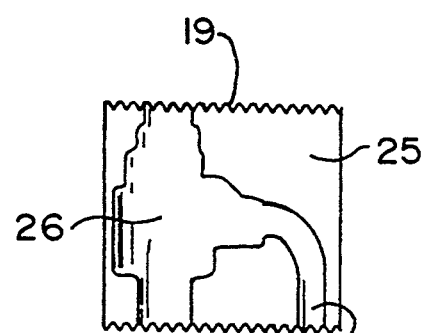
FIG. 8  FIG. 9  FIG. 10
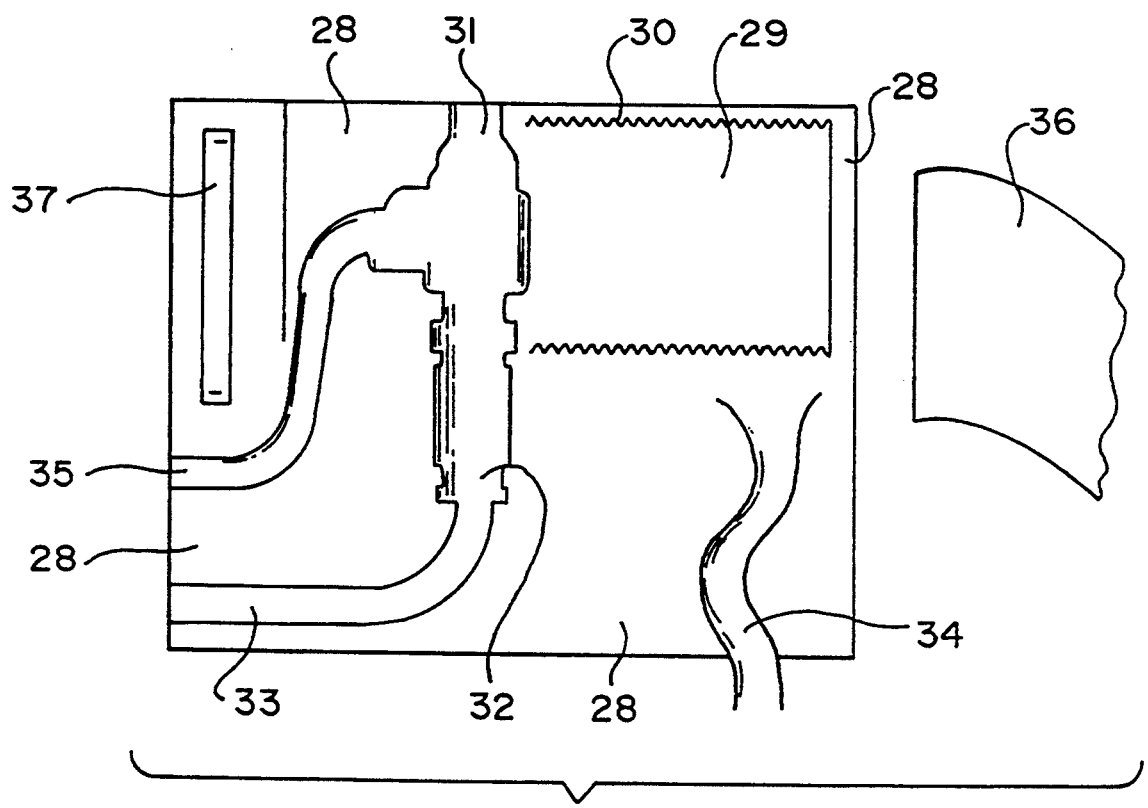
FIG. 11

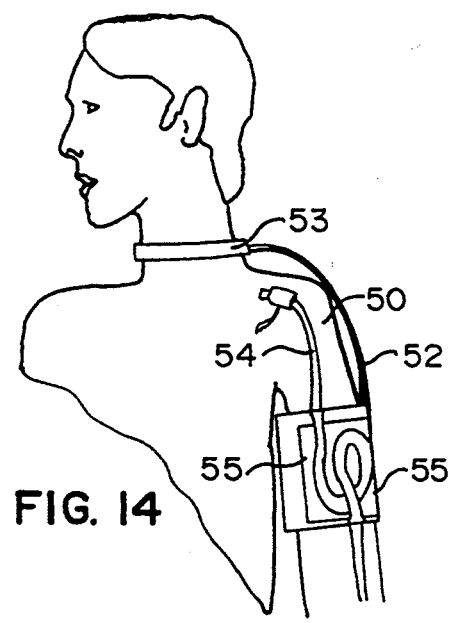
FIG. 14
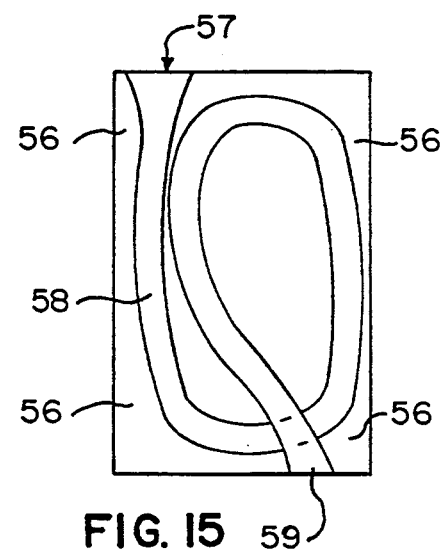
FIG. 15
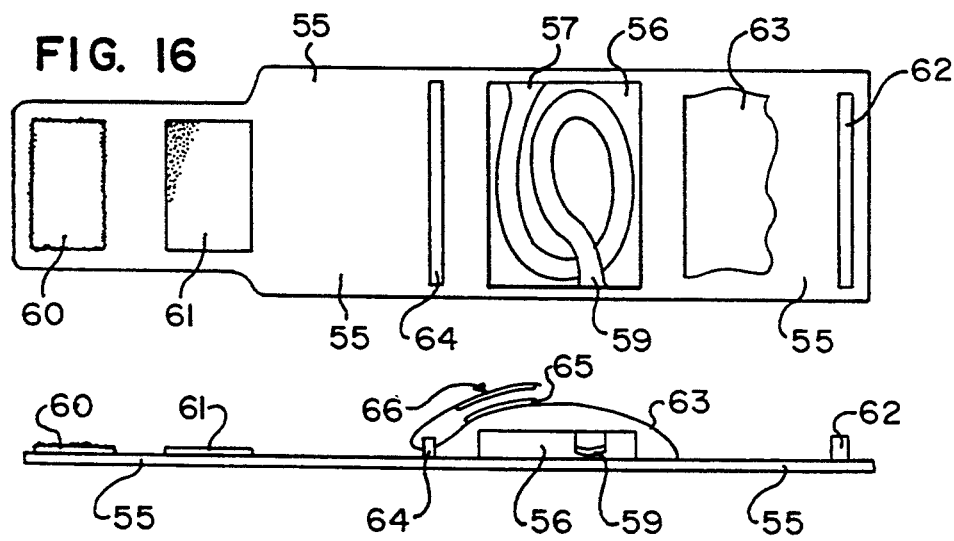
FIG. 16
FIG. 17

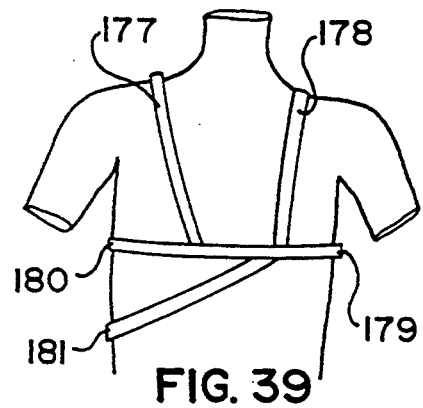
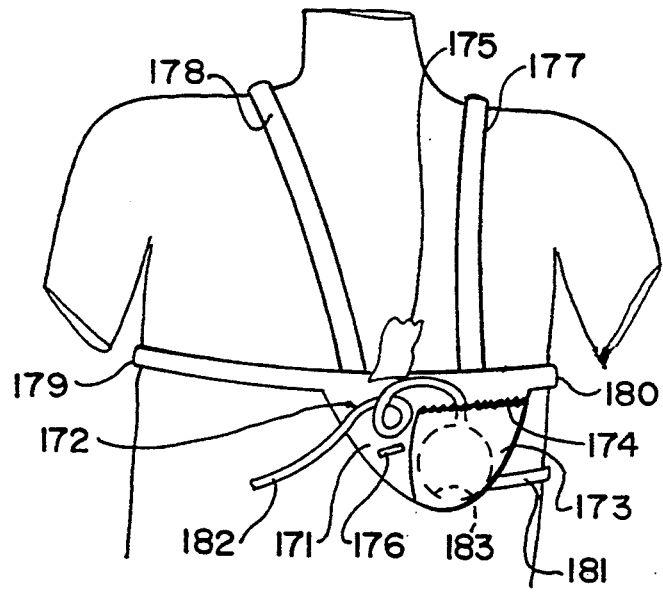
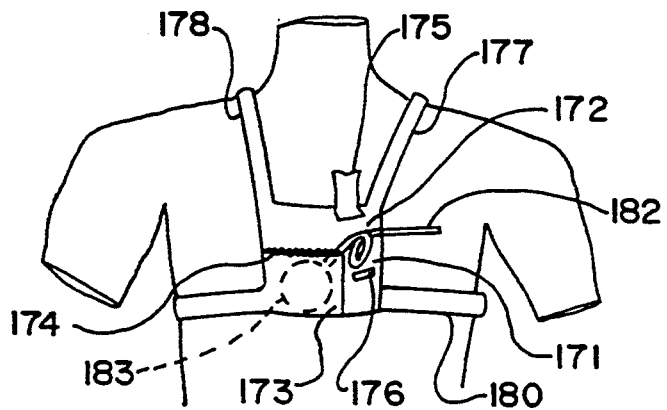

SPECIAL WRAPS, DILATORS AND FOLEY CATHETERS

FIELD OF THE INVENTION

This invention relates generally to a device for holding invasive treatment apparatus on the exterior of the body. Several embodiments are disclosed. Also disclosed are novel embodiments of dilators and Foley catheters.

BACKGROUND AND SUMMARY OF THE INVENTION

The use of various forms of tubular invasive device is a routine part of today's patient care and keeping them in place is a difficult job. The existing method of using adhesive tape is very primitive in my mind and has its own drawbacks. Not only may it not hold the tubular device in place appropriately, but also it may cause skin reactions, stick to hairs and pull them unwantedly. It is therefore desirable that the use of adhesive be diminished as much as possible.

This problem absorbed my attention and has led to my invention of a new technique that I believe will be very helpful in many cases and locations in holding different forms of tubular devices such as Swan Ganz catheters, arterial lines, arterial sheaths (after coronary angioplasty), Foley catheters, nasogastric tubes, wires of temporary pacemakers, etc. The various devices I introduce use a basic method that may be modified for the particular application. I also introduce two new dilators and a Foley catheter that I believe are much superior to presently available models and will be very helpful in future uses.

The general idea behind this invention is to use wrapping units to hold the tubing and wires and similar materials in place rather than adhesive tapes. These wrapping units are made from synthetic materials and fabrics that are available or can be made easily with some modification of present materials, such as those used in school bags or many disposable medical supplies. They can be cut, shaped, and trimmed to be used in arms, thighs and chest areas. They can be held in place by straps and/or narrow bands of adhesive. The straps are tightened and secured by Velcro TM patches, snaps, or adhesive surfaces. The wrap supports and holds a plastic tray that has, or holds plastic moldings with, cradles shaped to accept and hold invasive devices such as those mentioned earlier. These wrapping units keep the invasive devices securely in place by means of flaps, snaps, or plastic covers.

The new types of plastic dilators introduced here are smaller and more compact. They give a definite advantage, are much easier to handle, and can be used with the wrapping units. A special Foley catheter introduced here can also be held by a wrapping unit, making use of such device much easier. A small adaptor is also introduced to allow existing Foley catheters and nasogastric tubes to be used with the wrapping units.

The basic idea of this invention is to make wrapping units for holding various forms of tubular devices in place, which make it easier for patients and the medical staff, and which diminish the need for use of adhesive taping of these devices on skin. These units also diminish the chance of the devices being pulled or displaced easily. For elaboration of the routine problems that occur with the use of adhesive tapes, I feel it will be helpful to mention the following problems that commonly occur with adhesive tape.

The hair on the skin is a problem. Many times it prevents adequate sticking. Furthermore, when the tapes are pulled, they pull the hair causing a very painful reaction. I have witnessed many times when nurses warned patients of such pain and advised them to say "ouch" before removing the tapes. Many times the skin needs to be shaved for heavy taping in the groin area after cardiac catheterization and angioplasty. This is not easy and available every time. It has its own expense and problems, such as occasional infections and bleeding. Some adhesive materials for making the skin stickier may have bad odors and cause skin irritations. One of my own patients exemplified this problem: he had a large area of inflamed skin after the use of this material.

Therefore, it would be wise to diminish and avoid such problems as much as possible. The devices I introduce serve the purpose of holding many of the tubes, wires and catheters in place much easier and better and with much less use of tapes and adhesives.

The basic device, which I call Y. wrap, is made from a strong fabric of synthetic durable or disposable materials, such as used in handbags or some children's school bags. I would like to mention though that although I have not given any specific names for such materials, the state of the art relating to these materials is so advanced that making one for this purpose by experts seems to be very simple and possible. This material will be made in different shapes to fit the particular shapes and anatomy of different areas of the body where the arteries and veins are usually used for different purposes and different types of tubular devices need to be held in place. This wrap holds a plastic tray shaped to match and hold the tubular devices used to invade the body. The plastic tray has a molded shape that allows the particular tubular device to be seated securely on it and be removed when wanted. The molded shape matches the shade of the particular tubular device that is being used. In order for this tray to stay in place and be useful the following methods are used:

1.) In many devices the plastic tray is permanently embedded in the appropriate part of the wrap so as to be held in place securely.

2.) In some models one basic plastic tray "A" will be permanently embedded in the wrap and it will allow the insertion of a previously made molding of plastic "B" to be used. A part "B" will slide or attach to a part "A" by sliding inside it or by having small dents and pieces that will match and holds these parts together.

3.) A tray "A" is covered by a Velcro TM patch to accept and stick to a matching Velcro TM patch which is stuck to back of a part "B".

4.) A film of adhesive covers the back of part "B" and is protected by a plastic cover. The plastic cover is removed to expose the adhesive which is then stuck to a part "A".

5.) A flap attached to the wrap comes from one side of the tray to go over and cover the molded area that holds the tubular device and is tightened on the other side to hold the tubular device securely in the tray.

BRIEF DESCRIPTION OF THE DRAWINGS

FIG. 8 is a top plan view of an element that is used with the wrapping unit of FIG. 11.

FIG. 9 is a top plan view of another element that can be used with the wrapping unit of FIG. 11.

FIG. 10 is a top plan view of yet another element that can be used with the wrapping unit of FIG. 11.

FIG. 11 is a top plan view of a central portion of another embodiment of wrapping unit.

FIG. 14 is a perspective view illustrating a further embodiment of wrapping unit in use.

FIG. 15 is a plan view of a portion of the wrapping unit of FIG. 14 on an enlarged scale.

FIG. 16 is a plan view, slightly enlarged, showing more detail of the wrapping unit of FIG. 14 and prior to use.

FIG. 17 is a front view of FIG. 16, illustrating a slightly different position of certain portions of the wrapping unit.

FIG. 38 is a view illustrating usage of a still further embodiment of wrapping unit.

FIG. 39 is a rear view of FIG. 38.

FIG. 40 is a view illustrating usage of still another embodiment of wrapping unit.

FIGS. 1-4 show a first embodiment of wrapping unit. It comprises a wrap 1, like a wristband, 3 to 4 cm. wide, or even wider, depending on where it is to be used. Wrap 1 has ends 3 and 4 (cut short in FIG. 1 for illustrative purposes) which will come together to be separably secured by Velcro TM patches 9A and 10A, as in FIG. 2. Wrap 1 has a flat plastic surface area 2 having multiple raised parts 10 to allow a tube T to pass through space between them, as in FIG. 4. Tube T and this area are then covered by a strap, or a flap, 5. Flap 5 is pulled through a bridge 6 to make it tight and then to have its own Velcro TM patches 7 and 8 shown in FIGS. 1 and 2 to stick and hold this flap in place.

This wrapping unit, when functional, will hold tube T so as to prevent it from being pulled easily through the wrap, since pulling will meet the resistance build up in the unit by the S-shaped path which the tube takes through the unit.

A pocket 11 made from a clear plastic on the flap, will allow small piece of paper (not shown) to be inserted to keep a record of the time when an IV was started through tube T and another pocket 12 made from same kind of clear plastic will allow information (not shown) about the patient to be inserted and even to be used as a patient's ID band as well. A special end part 12a of pocket 12 will prevent the paper containing the patient information from being removed easily. When this wrapping unit is used for holding the ID of a patient, then ends 3 and 4 will be permanently fixed to each other with irreversible snaps.

Figure 22:
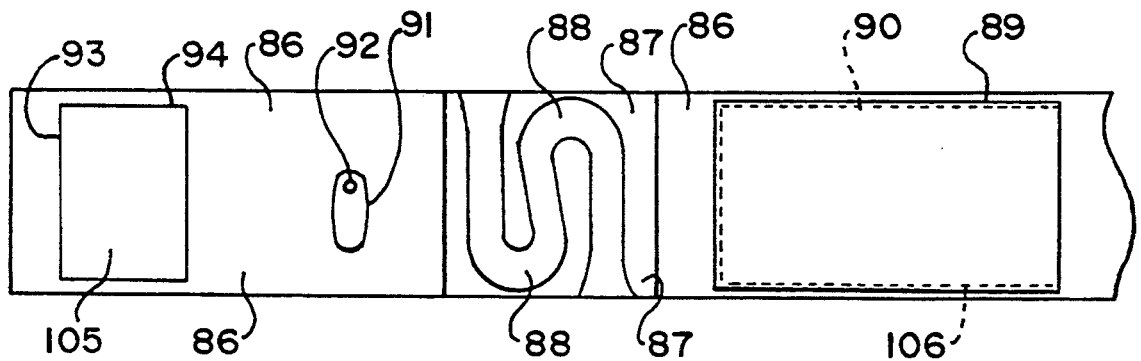
FIG. 22 is a top plan view of yet another embodiment of wrapping unit, with certain portions removed.
Figure 23:
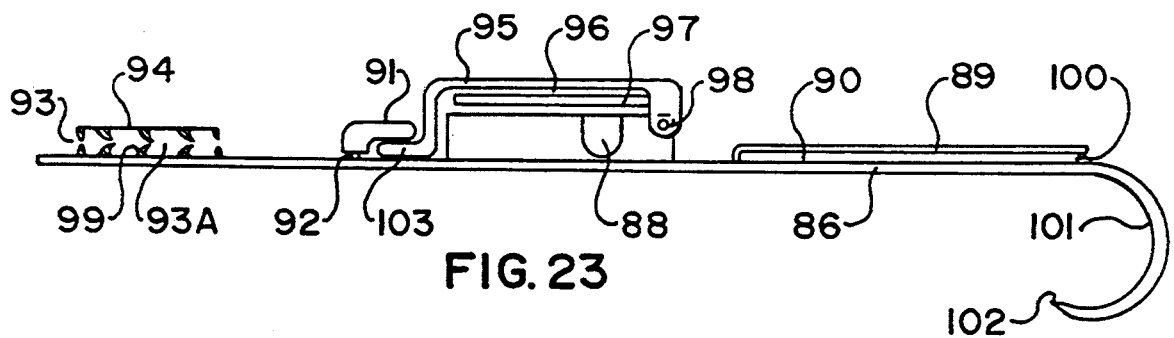
FIG. 23 is a front view of the wrapping unit of FIG. 22 with a portion in cross section.
Figure 24:
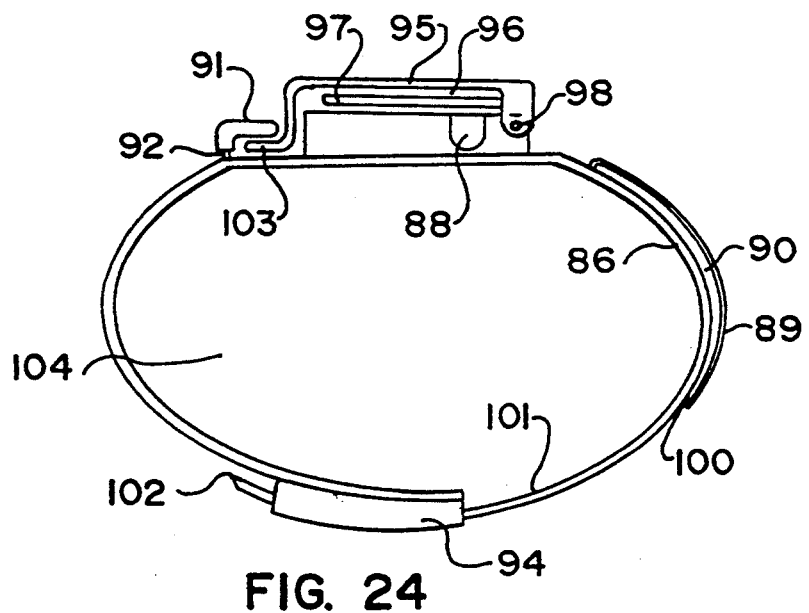
FIG. 24 is similar to FIG. 23 in a position of usage.

FIGS. 22-24 show a similar wrapping unit which has a slightly different means for holding tube T. Here the place for holding tube T is a small box-like plastic tray 87 embedded in a wrap 86. This plastic tray has a canal 88 to accept tube T and then to be covered by a cover 95 which is connected to the tray by a hinge 98. Cover 95 is held in place by use of a latch 91 connected to the base of the tray by a short pole 92 about which the latch can rotate. FIGS. 23 and 24 show the latch rotated to overlie an edge 103 of cover 95 opposite hinge 98. Cover 95 has a small dividing wall 97 inside it to make a narrow pocket 96 for insertion of a piece of paper (not shown) in order to provide a record of the time of the IV insertion on the patient. A space 90 is covered by clear plastic 89. A dotted line 106 shows the inside border of the plastic 89. This space 90 is for insertion of a patient's ID information and an indentation 100 is to prevent the paper which contains the information (not shown) from being removed easily. Wrap 86 has a free part 101 that ends at 102. This part will go through a box 94 made from plastic and having an opening 93. Inside this box spears 99 are designed to make the area between them 93A a one-way direction for end 102 when it goes through. This technique will prevent a patient from removing this unit unless the wrap is cut.

FIG. 24 shows this wrapping unit in place like a wristwatch, the patient's wrist being in area 104.

This basic idea with some modification can be used to hold temporary pacemaker wires as well as Swan Ganz catheters, Foley catheters, arterial lines, and other tubular devices and wires that need to be held in place properly. These wrapping units will make this job much easier and better. Naturally, the size of a wrapping unit will depend on the area and part of the body where it is to be used, as well as the size of a patient.

Having this background and more basic information in mind, I would like to introduce some more particular wrapping units that are using the same general idea.

The usual routine to support a functioning arterial sheath in place after coronary angioplasty is to insert a piece of a hard tubing called "dilator" inside the arterial sheath to prevent its collapse and occlusion. This is also used to connect a monitoring system for monitoring the patient's blood pressure. After insertion of the dilator inside the sheath, its free end is connected to a three-way stopcock, and this unit is fixed on the skin with one suture to prevent it from being pulled. This is done before the patient is moved from the table in the catheterization lab. (The information I provide here is based on my observations in a very active cardiology unit of a major American teaching hospital, William Beaumont Hospital, Royal Oak, Mich., over three years.)

In my view, this whole unit having a three-way stopcock connected to a dilator and sheath is very bulky and difficult to handle. It involves much work that can be avoided if replaced with a better unit that I suggest. The unit I have designed I call here: Special Dilator. It combines the dilator and three-way stopcock together to make a unit that is more compact and much easier to use. The combination is made by cutting the distal end of the dilator and connecting it to the front end of the three-way stopcock. Naturally, this unit will eliminate the part that is not needed (the base of dilator), and will reduce the job of connecting those two parts together, which will diminish some job and the total volume of those parts.

Figure 4:
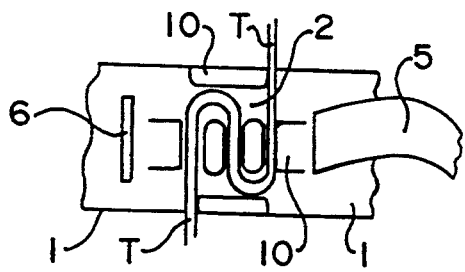
FIG. 4 is a view similar to FIG. 1, but on a reduced scale, showing a tube in association with the wrapping unit of FIG. 1.
Figure 4A:
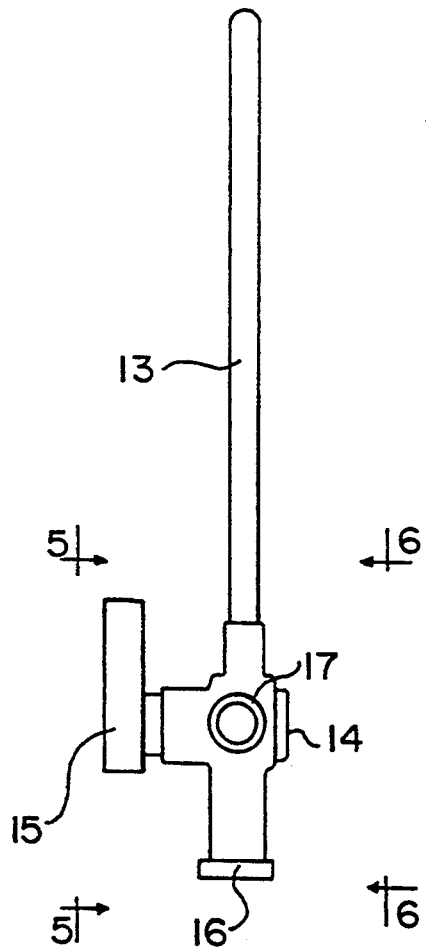
FIG. 4A is a top plan view of a novel dilator with which a wrapping unit may be advantageously used.
Figure 5:
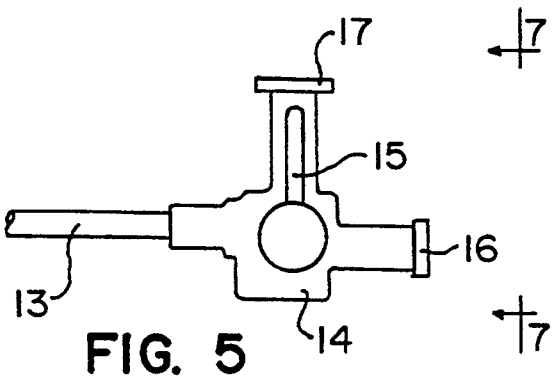
FIG. 5 is a partial left side view of FIG. 4A as taken in the direction of arrows 5—5 in FIG. 4A.
Figure 6:
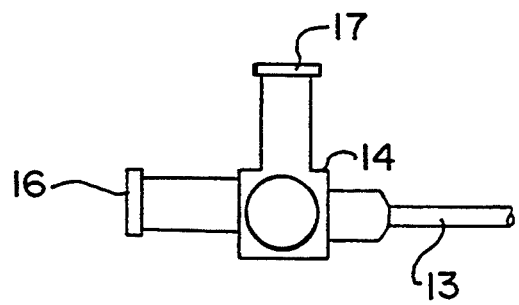
FIG. 6 is a partial right side view of FIG. 4A as taken in the direction of arrows 6—6 in FIG. 4A.
Figure 7:
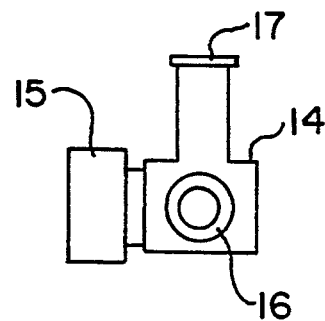
FIG. 7 is a view in the direction of arrows 7—7 in FIG. 5.

My unit, shown in FIG. 4A, is smaller and can be handled easier. The piece 13 is a part made from the hard plastic that fits inside the sheath (not shown here). The three-way stopcock 14 has a handle 15 and an opening in the top 17 that can accept any universal IV end that can be screwed to it in conventional way. The opening in the end 16 also accepts any universal IV, and in general is connected to a pressure line to measure the pressure. FIGS. 5, 6 and 7 show different views of the Special Dilator. The handle points to the opening which will be closed to circulation.

Figures 4B, 5A:
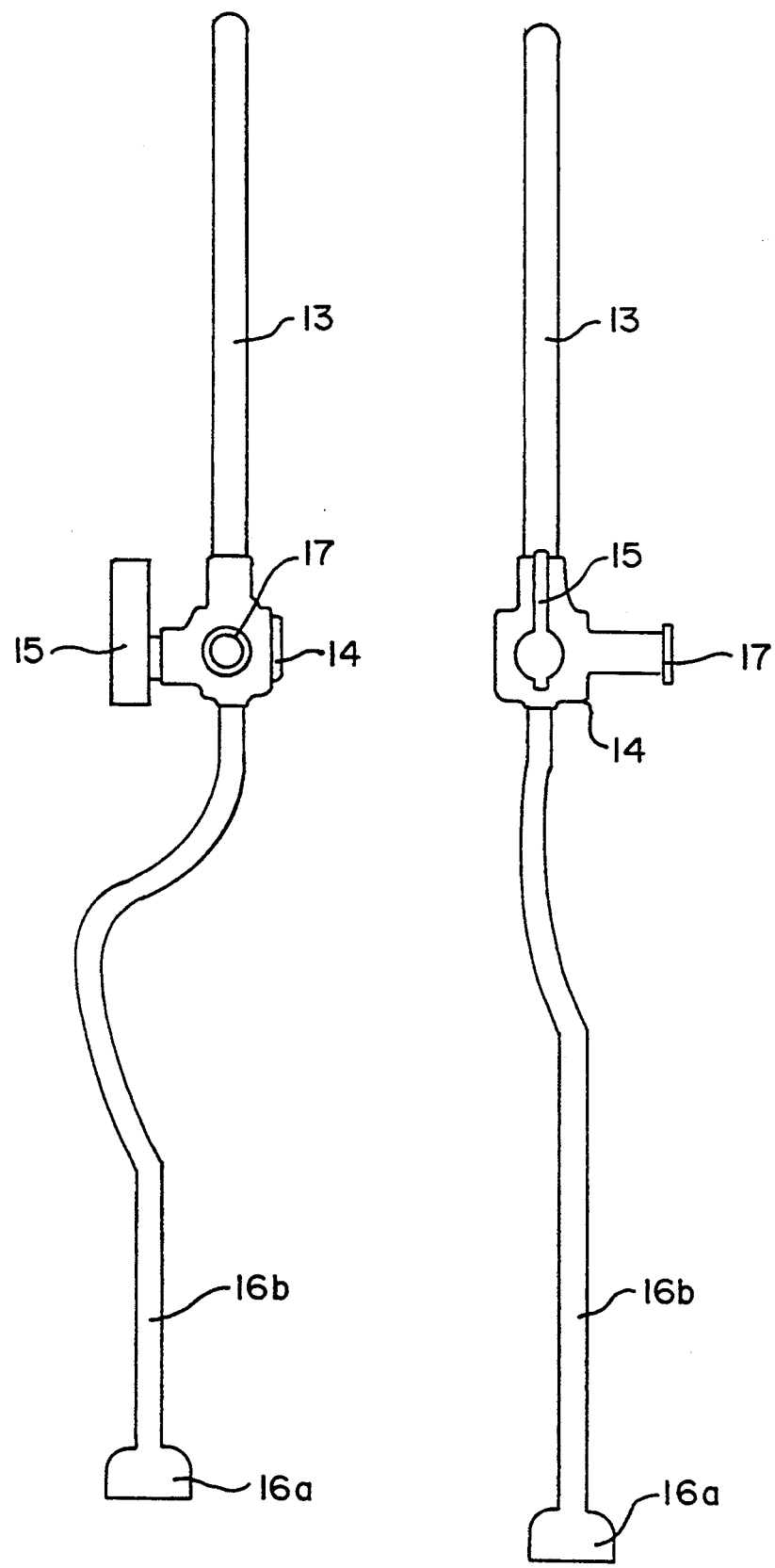
FIG. 4B is a top plan view of a modified form of dilator.
FIG. 5A is a left side view of FIG. 4B.

Another version of Special Dilator which I call here "Special Dilator—version B" is shown in FIGS. 4B and 5A. It is made by connecting the free end of the three-way stopcock directly to a pressure tube of 5 to 24 inches long or so. This unit will conduct the pressure away from the patient, and the three-way stopcock is connected to end of this tube far away. This allows the unit to be connected to another pressure tube farther away from the patient and finally to a transducer so that work on a patient's body area will be less, allowing him to rest more.

The hard tip 13 is connected to a three-way stopcock 14 having a handle 15. An opening for connecting to an IV tubing is shown at 17. The pressure tubing is shown at 16b and ends at 16a in a universal ending that will accept a pressure line (not shown) connected to it.

Having mentioned the Special Dilator, I would like to explain how the sheaths can be held in place with ease and stability. FIG. 8 shows a cradle 21 made from plastic that will match and accept the base of a sheath which can be placed inside it easily and only with slight pressure. The saw tooth 19 is designed to match and fit inside a saw tooth 30, and the part 20 which contains the cradle will sit in an area 29 of the tray shown in FIG. 11. The same is true about a part 22 shown in FIG. 9. Part 22 has a cradle 23 to accept the left surface of a sheath and 24 is a channel to accept the tubing of the sheath.

FIG. 10 shows a part 25 for the right face of a sheath (usually the venous sheath when the right groin is used for intervention and tube insertions), part 25 having a cradle 26 and sawtooth indentations 19 will match sawtooth 30 so that part 25 can sit in area 29. A canal 27 is to hold the tubing of the sheath. I would like to mention that these parts 22, 25 are pieces of plastic, that either one of them can be chosen to be placed in the area 29 of FIG. 11. FIG. 11 shows a plastic tray 28 made with different cradles to accept the part of the sheath used for angioplasty and are left in groin after the procedure is completed.

It may be helpful to briefly explain how this unit can be beneficial and used. As mentioned earlier, usually after the angioplasty of coronary arteries (opening of the heart vessels by balloon), there is an arterial sheath which is left inside the artery and a venous sheath which is left inside the vein. The venous sheath usually lays to the right side of the arterial sheath when the right groin is used. Then, the arterial sheath is sutured to skin, in order to prevent its accidental pulling.

Figure 12:
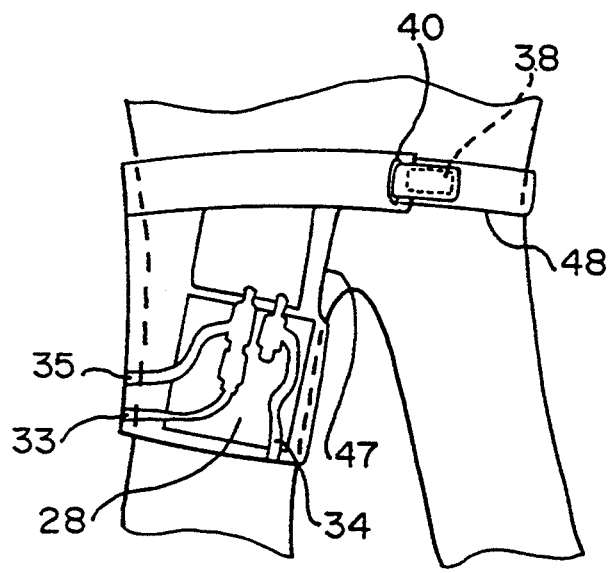
FIG. 12 is a view showing usage of the wrapping unit of FIG. 11.

What I introduce is to have a tray such as the one shown in FIG. 11 to hold the sheaths in place. This tray will be laid flat on skin and under the arterial and venous sheaths as in FIG. 12. When this unit is in place, then the free end of the arterial sheath will sit inside cradle 31 and its tubing will fit into 35. The dilator fits inside the arterial sheath as well with its base fitting in cradle 32 and its tubing fitting in canal 33. The piece shown in FIG. 10 sits in area 29 with sawtooth 19 matching sawtooth 30. The right surface of the end of venous sheath fits with slight pressure in cradle 26 and its tubing lays in canal 27. The continuation of the tubing lays in canal 34. This tray is made to be embedded in a place designed for it on the surface of a wrap such as shown in FIG. 12. When the dilators are in place, a flap 36 (only whose base is shown in FIG. 11) goes over the bases of the sheaths, and then through bridge 37 and finally, the flap's end attaches to a Velcro TM patch made for this purpose to hold it in place. In my view, when the dilator sheaths are inside this wrapping unit, they are much safer and sturdier than having a tie with one stitch on the skin, and then taped on the thigh. By using this wrap, there is no need for suturing and much less taping needs to be done. A narrow band of non-irritating glue may be used in upper and in the back rim of the wrap to hold the edge of the wrap in the exact place desired. This will be discussed further later in this application.

Figure 13:
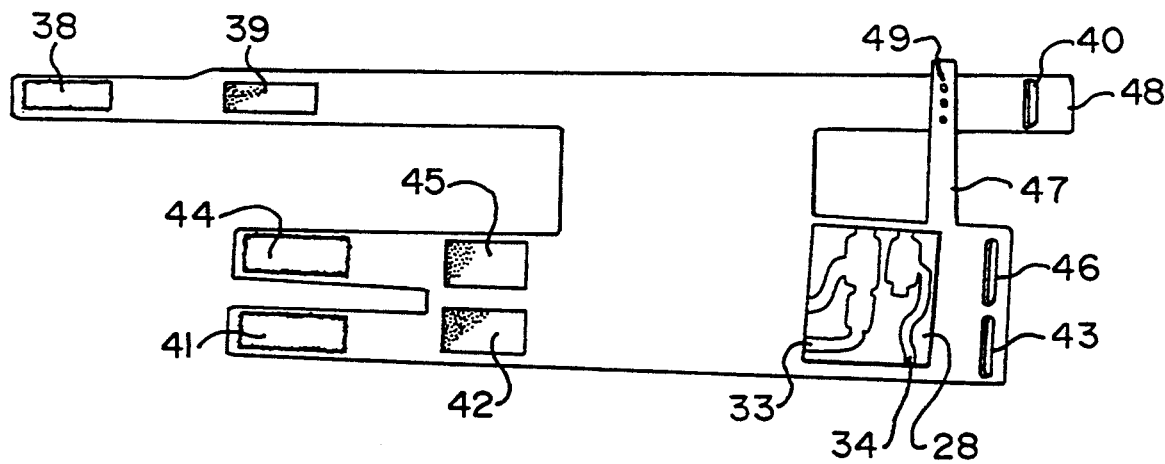
FIG. 13 is a plan view of the wrapping unit of FIG. 12 prior to usage.

FIG. 12 shows schematically the general view of the Y. device for groin. This shows where the plastic tray will be situated and its place in the wrap. FIG. 13 shows the front view of the Y. device for groin when it is spread on a surface. In this view, the belt for the girdle is in the top 48 and its end has Velcro TM patches 38 and 39. When the wrap is placed, patch 38 goes through bridge 40 and makes a U-turn to come and attach to patch 39; end 41 goes through bridge 43 and back to stick to matching patch 42, and end 44 goes through bridge 46 to make a U-turn and stick to matching patch 45. A strap 47 will attach the groin wrap to the girdle wrap to keep it more stable, and the height of the strap 47 can be adjusted with use of snaps 49. A film of non-irritating glue may be used to allow sticking the upper edge of this unit to the skin of groin. This film of adhesive will be like a rim, located about 0.5 to 1 cm. lower than the upper edge of the wrap and in the side which will face the skin. (This adhesive film will be covered by a plastic cover that is removed for exposing the glued surface.)

FIGS. 14–17 relate to a Y. device for arm. It is made from a wrap 55 that goes around the upper arm 50, the ends of this wrap coming together with use of Velcro TM or snaps or glue. A strap 53 goes around the neck like a collar and a piece of strap 52 comes from that collar to attach to the upper body of this arm wrap to prevent it from falling down. It may, however, be eliminated in some models, since the anatomy of the arm itself may serve this purpose.

On a front to lateral side of wrap 55, a plastic tray 56 is fixed and has a canal 58 for a Swan Ganz catheter or a temporary pacemaker wire to be inserted inside it. A flap 63 goes over them and through bridge 64 and has a patch 66 to stick to a Velcro TM patch 65 and to keep the contents of the tray from falling. FIG. 14 shows this unit in place. A Swan Ganz catheter 54 goes inside canal 58. One end of the canal is 57, and the other end is 59. The end of wrap 55 goes through a bridge 62 to make a U-turn and a Velcro TM patch 60 to stick to a matching patch 61. A band of non-irritating adhesive may be used to prevent motion of this unit on the arm, being covered by a plastic cover similar to the one mentioned earlier.

FIGS. 18–21 relate to wrapping units for Foley catheters, which I call the D. wrap. The catheters that are inserted into the bladder are, I believe, often neglected. They are either left alone and can move freely, or they are taped on skin with the problems that comes with taping. Using tight bands around the thigh is unwise, since they are bad for circulation and may cause blood clot formation in the thigh and leg area. Having thus background in mind, it will be somewhat easy to see how my invention comes to play its important role in this regard.

The device I introduce allows a Foley catheter to be held in place with the use of a wrap. This wrap goes around the thigh and is held in place, and is prevented from falling by its connection to a belt around the girdle. Using this wrap, the Foley catheter goes through a canal and then is covered by a flap that holds it securely in place. Although an ordinary Foley catheter can be used with this wrap, it will be better to use a "special Foley catheter", which I have introduced and will explain later. An adaptor is also very helpful in this regard, and I will mention it later.

Figure 18:
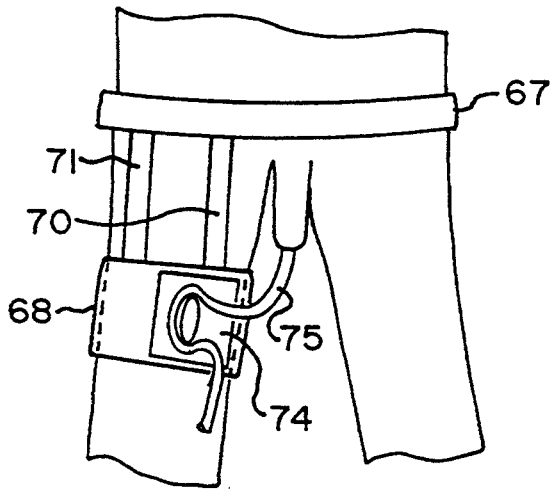
FIG. 18 is a view of another wrapping unit in use.

This wrap, shown in FIG. 18, is basically made from a disposable or durable strap 67 that goes around the girdle and with two straps 70 and 71, it connects to a thigh wrap 68. This thigh wrap has a plastic tray 74 embedded in it, and the tray has a canal that allows a Foley catheter 75 to sit in place inside it, and then be covered by a flap similar to flap 63 shown in FIGS. 16 and 17, or by a cover over it like cover 95 in FIGS. 23 and 24.

Figure 19:
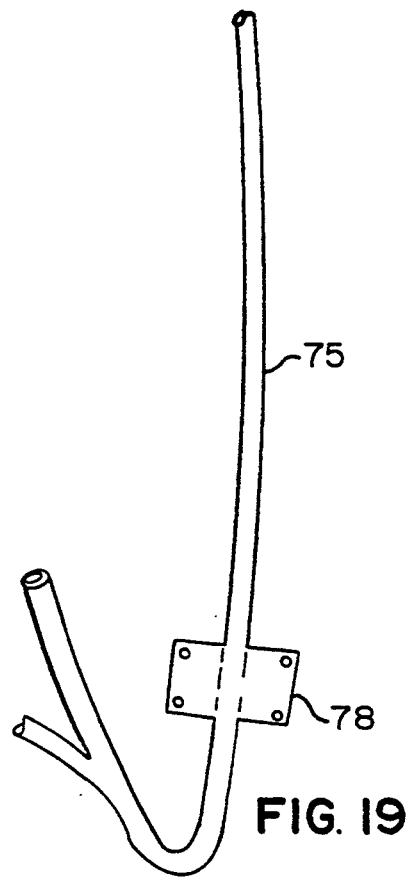
FIG. 19 is a plan view of an embodiment of Foley catheter.

FIG. 19 shows the "special Foley catheter" 75 that makes the job of fixing a Foley catheter in the thigh area much easier. The ordinary Foley catheter does not have any special place for taping and what the nurses usually do is stick tape around it. This is not the best way to do the job though, and the change I introduce to make a "special Foley catheter" will fill this gap and offer a distinct advantage. The "special Foley catheter" has a flat part 78 made from non-irritating plastic (the same material that the Foley catheter is made of). This part has a rectangular shape with four holes in the corners. Part 78 has a flat face at its back to be held toward the skin. I believe that even if someone decides to tape a Foley catheter rather than using the wrapping unit, the "special Foley catheter" is the best way to do it, using flat part 78 for this purpose. The shape of part 78 can be circular or similar shapes. In order to use an ordinary Foley catheter, a special adaptor will be useful to convert it into a "special Foley catheter".

Figure 20:
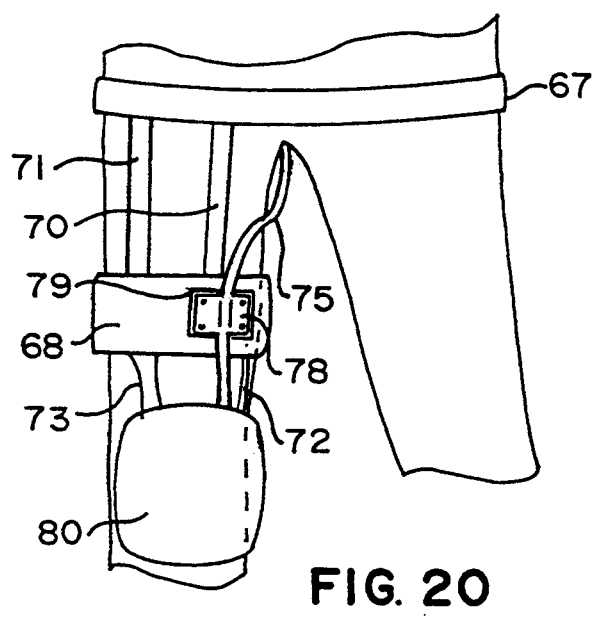
FIG. 20 is a view illustrating use of a modified form of the Foley catheter of FIG. 19.

FIG. 20 shows another version of Y. wrap for holding a Foley catheter. This wrap is very similar to one mentioned in FIG. 18 except it is made to accept and be used with "special Foley catheters", or a regular Foley catheter with an adaptor attached to it. In this unit, tray 79 is smaller than tray 74, and tray 79 will accept part 78. It is covered either by a flap similar to flap 81 shown in FIG. 21 or by a cover such as cover 95. A urine bag 80 is attached to the thigh wrap with straps 72 and 73.

Figure 21:
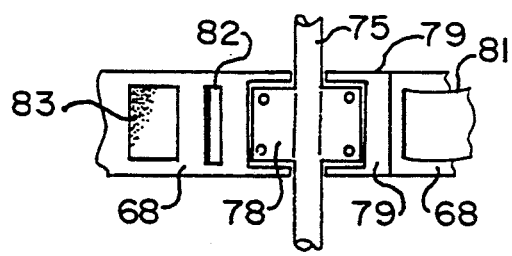
FIG. 21 is a plan view showing detail of the association of the Foley catheter with the wrapping unit.

FIG. 21 shows tray 79 in more detail. The tray is made from plastic embedded in strap 68. It has a cradle that matches and accepts the part 78 shown in FIG. 19. Then a strap 81 goes over part 78, through small bridge 82, and its end covered by a patch (not shown here) to stick to its matching Velcro TM patch 83.

Figure 25:
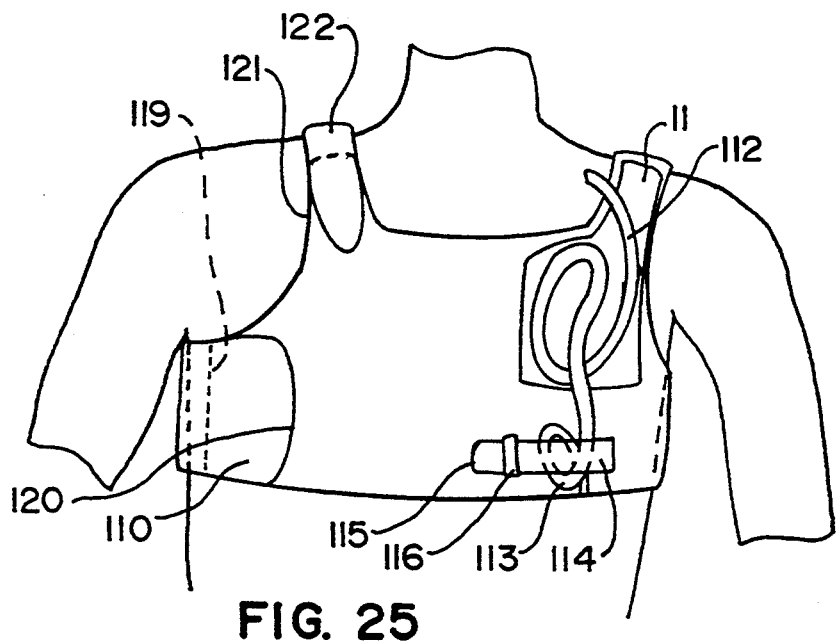
FIG. 25 is a view illustrating usage of yet another embodiment of wrapping unit.

Y. device for holding tubing, wires and devices in the chest area is shown in FIG. 25. The basic wrap will be made in the shape of a vest from synthetic materials which are strong and non-stretchable. It may have a soft fabric lining to prevent irritation of skin, and also to have comfortable rims. This vest will stay in place due to its special shape, and has flaps that will stick to each other. Two flaps, one 121 from the front which connects to flap 122 coming from the back, and flap 119 from the right end of the front piece connecting to flap 120 coming from the back. These will connect with use of Velcro TM patches, snaps, or adhesives. This vest will give enough space to hold many size trays that can be positioned differently with use of Velcro TM patches or adhesives to its surface to hold different wires or tubes. In this view, tray 11 is used to hold the IV tubing 112, inserted to left subclavian area or pacemaker wire or Swan Ganz catheter, coming from left subclavian area. These tubes will go inside the canals that will match their size. For example, for temporary pacemaker wires, it will have a narrow canal for a Swan Ganz catheter, it will have wider canal, and for a double lumen subclavian catheter, it will have a matching canal too. They will be held in place by a flap or plastic cover over the tray. Some extra flaps such as 114 will be positioned that will allow to hold more tubing such as 113. The end of this flap will go through a bridge 116 to attach over a Velcro TM patch or a snap in area 115. Different plastic trays with different sizes and shapes may be attached to different areas of this wrap with use of adhesives in their back and this will expand the use of such wrap significantly, and will provide many options. This unit can be used for many purposes, procedures, and surgeries.

Figure 26:
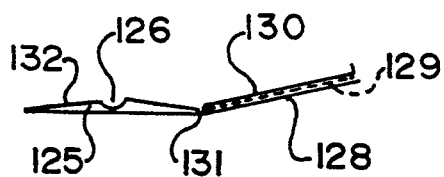
FIG. 26 is a front elevational view of an element that is used to adapt a conventional Foley catheter for use with a wrapping unit.
Figure 27:
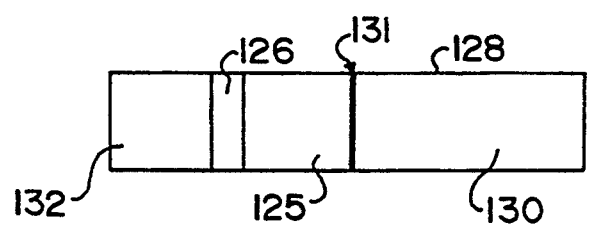
FIG. 27 is a top plan view of FIG. 26 on a slightly enlarged scale.
Figure 28:
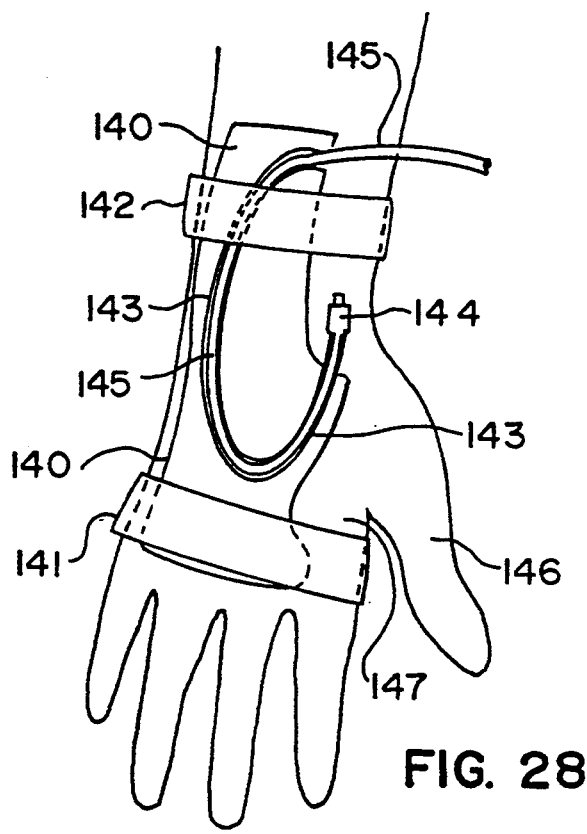
FIG. 28 is a plan view illustrating usage of still one more embodiment of wrapping unit without its cover.

In order to use the present Foley catheters or nasogastric tubes with the wraps, I have designed a small adaptor that is shown in FIGS. 26 and 27. This adaptor holds a Foley catheter or nasogastric tube due to shape and size of its matching lumen, as well as glue which is in the plastic cover that goes over them. After assembly of this adaptor, then a Foley catheter or nasogastric tube can be attached to the appropriate wrap. The adaptor comprises a part 125 made from plastic and having groove 126.

A matching part 128 can bend along a line 131 and has a layer of glue 129 covered by a plastic cover 130. The plastic cover 130 is removed to expose the adhesive 129, and then part 128 is stuck on a surface 132 of part 125 to cover the Foley catheter inside groove 126. This adaptor has a general size of about 3–5 cms. with thickness of about 2 to 5 mm. The use of these soft non-irritant parts will allow the Foley catheters and nasogastric and similar tubes to be taped to the skin much easier and sturdier than the tube alone.

FIGS. 28–31 show a D. wrap for a wrist arterial line. It comprises a plastic tray 140 that fits about the upper third of the palm, leaving the base of the big thumb 146 free, and also covering about 7 to 10 cms. of the lower anterior part of the wrist. The face of this has a surface like a cradle that matches the anatomy of the lower wrist and upper hand 147, to allow those parts to sit inside it. The surface which faces the hand and wrist will be covered with a soft cover such as a layer of sponge and/or fabric, to make a soft cushion for the skin to touch.

The other face of tray 140 has a canal 143 that holds the tubing of an arterial line 145 and allows insertion into the wrist artery at 144. The tubing is held inside canal 143 by use of a) flaps, b) plastic cover, or c) snaps. The tray is held in place on the palm and wrist by straps 141 and 142. The advantage of this device is that it prevents accidental excessive motion of the arterial line inside the small radial artery and decreases the possibility of damage to the artery.

Figure 29:
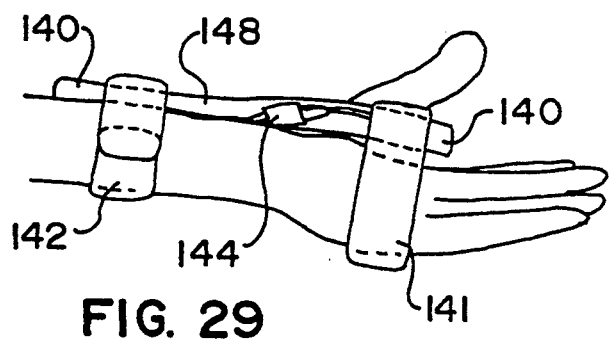
FIG. 29 is a side elevational view of FIG. 28 with its cover.

FIG. 29 shows the Y. wrap in use with the arterial line in place and the tray covered by another plastic cover 148. The whole unit is held in place by straps 141 and 142.

Figure 30:
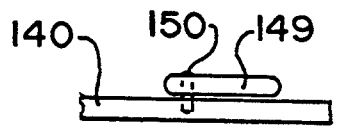
FIG. 30 is a fragmentary side view illustrating a modified form of wrapping unit of FIG. 28.
Figure 31:
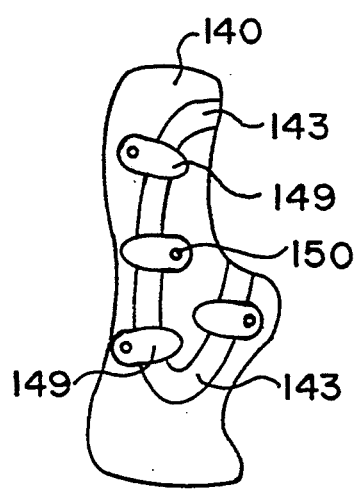
FIG. 31 is a fragmentary plan view illustrating the modified form of wrapping unit of FIG. 28.

FIGS. 30 and 31 show how latches 149 may be used to hold the tubing in place. Latches 149 are connected to the tray by short poles 150 that allow the latches to turn. FIG. 31 shows latches 149 turned to hold the arterial line in place, eliminating use of a plastic cover 148 for this purpose.

FIGS. 32–36 show a universal wrap. In order to be able to use the above mentioned wraps with different catheters and arterial lines, I have designed a technique and wraps that allow for and facilitate use of different trays and moldings with the wrap. For this purpose, the basic wrap can be made as described earlier; however the plastic tray of the wrap has a flat surface with a trim that will allow different plastic moldings and cradles to be inserted, attached or glued to it. By this technique, there would be no need to have a whole different unit to fit every different tubing and dilator. As long as the matching cradle is available then the wrap can be used with the tubing matching it.

Figure 32:
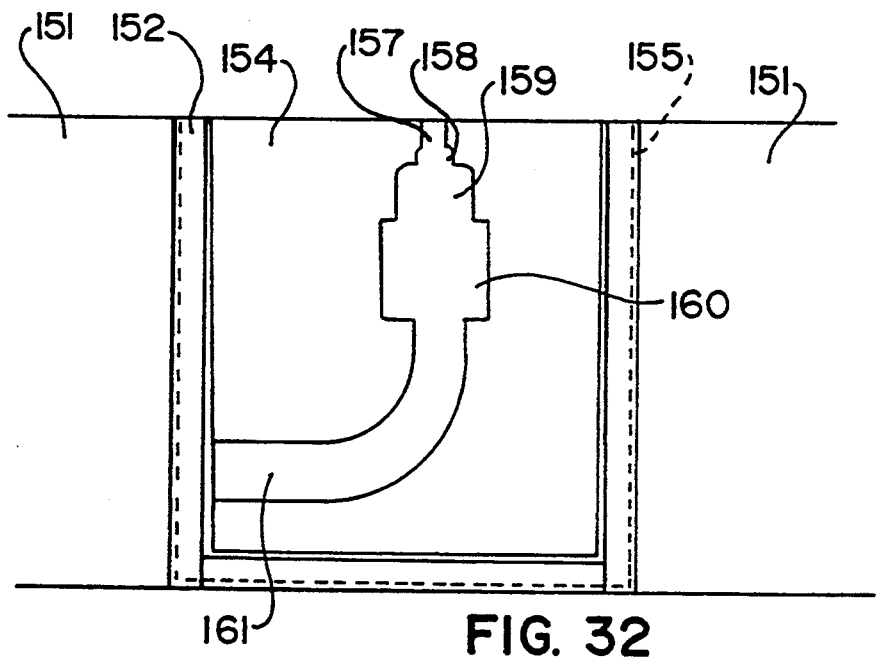
FIG. 32 is a partial top plan view of a modified form of wrapping unit.
Figure 33:
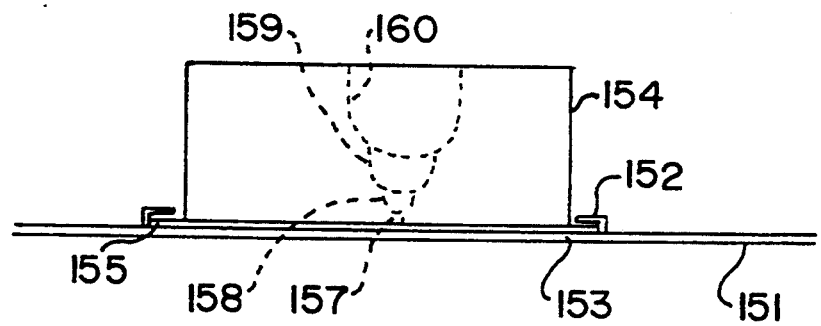
FIG. 33 is a front view of FIG. 32.

FIG. 32 shows one sample of such unit. This view shows a universal wrap for the groin. A basic plastic tray 153 has a trim 152 which makes it possible to slide a plastic molding and cradle 154 inside it. Wrap 151 holds plastic tray 153, and it (the tray) allows the part 154 to slide inside it. A broken line 155 shows the rim of the base of part 154. Part 154 has a cradle for placement of an arterial line in the groin. The tube of the arterial line, which is thin, is positioned in section 157. Its wider part in section 158. The base of the arterial line is placed in section 159. The tip of a connecting pressure line is placed in section 160, and the tubing fits in a canal 161.

Figure 34:
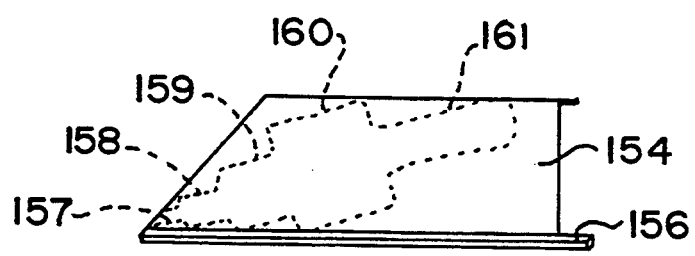
FIG. 34 is a left side elevational view of FIG. 32.
Figure 35:
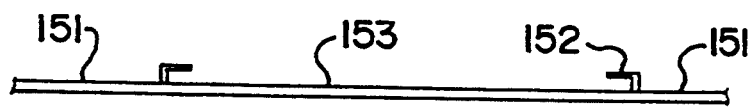
FIG. 35 is a view similar to FIG. 32, but with a portion omitted for illustrative purposes.
Figure 36:
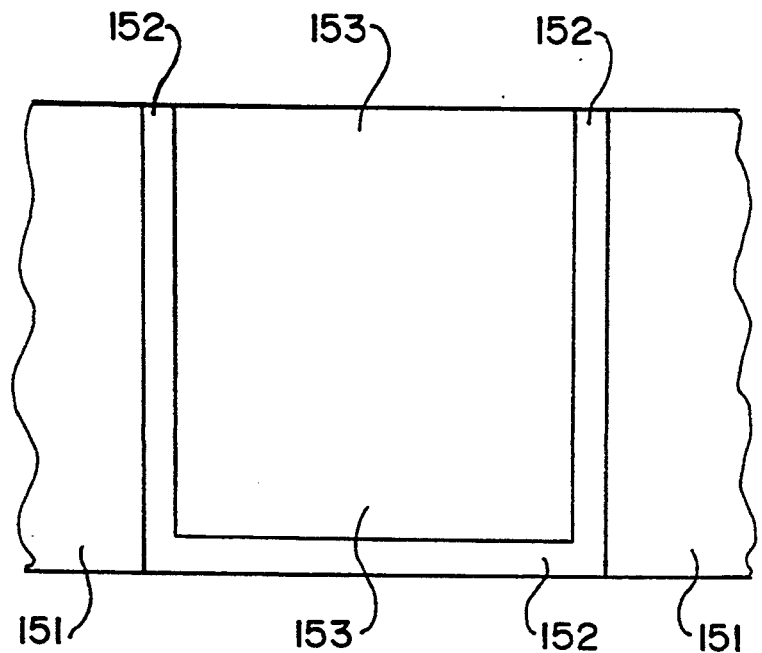
FIG. 36 is a top plan view of FIG. 35.

The view of FIG. 34 shows the base 156 of part 154 extended to make the rim 155.

Figure 37:
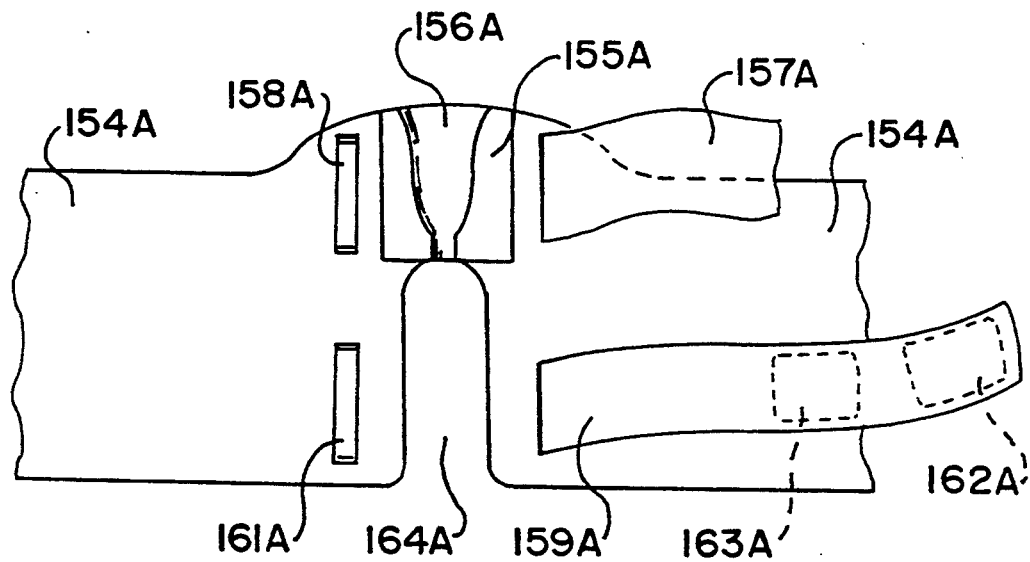
FIG. 37 is a fragmentary plan view of still one more embodiment of wrapping unit.

FIG. 37 relates to a Y. wrap for the neck. There are times that a catheter is inserted inside a vein in the neck called jugular vein. Holding this catheter in place is also hard and usually done with heavy taping of the catheter to the neck. In order to make the job of holding this catheter and IV line in place easier, I designed Y. wrap for the neck. The wrap is made from synthetic material like the groin wrap except it is covered by a soft non-irritating cover to prevent irritation and hurting the skin of neck. Wrap 154A is wrapped around the neck to stand like a collar so that the open area 164A is over the jugular vein area. The base of the jugular catheter will sit inside a matching cradle 156A. A plastic tray 155A surrounds cradle 156A. When this wrap is in place, a flap 157A (only the base part of it is shown here) will go through a bridge 158A and to be fixed with patches of Velcro TM or adhesive in its own back. This will hold the base of the jugular line in place. A strap 159A goes through a bridge 161A to make a U-turn and its Velcro TM patch 162A attaches to a patch 163A to hold this part tight in place. An adhesive surface may be also used to keep this wrap in a desired place on the neck.

FIGS. 38 and 39 relate to a Y. wrap for holding tubing after some abdominal surgeries. In some abdominal surgeries such as gallbladder surgery, or diverticulitis, a tube is left in place; in my observation, it is not kept appropriately in place. Heavy taping or fastening it to the robe of a patient by means of a safety pin are used for keeping it in place. This is not the best way in my mind for doing such a job, and use of a modified wrap will be very useful in this regard. The wrap I introduce is shown in FIG. 38.

Figure 1:
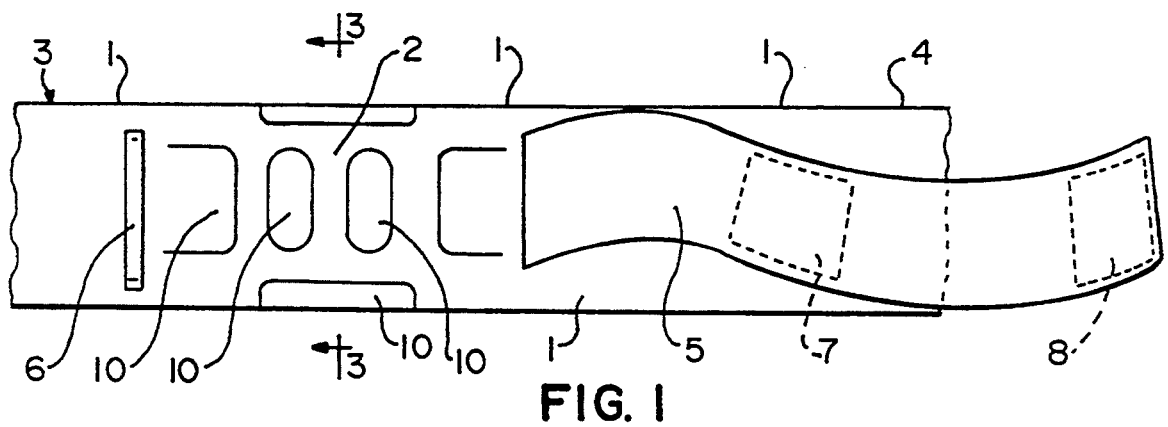
FIG. 1 is a top plan view of a central portion of a first embodiment of wrapping unit according to the present invention.
Figure 2:
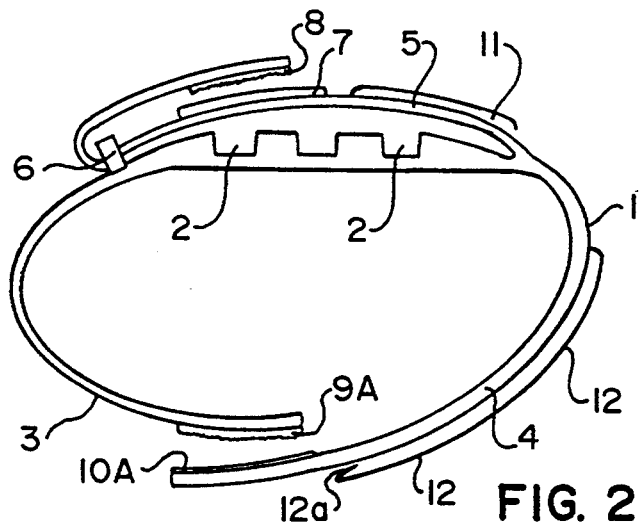
FIG. 2 is a full front view of FIG. 1 shown approximately in a position of use.
Figure 3:
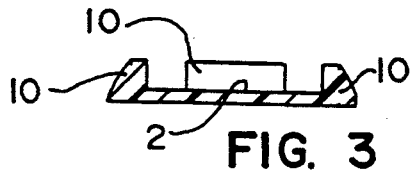
FIG. 3 is a transverse cross section taken in the direction of arrows 3—3 in FIG. 1.

This will be made from synthetic materials that will be soft and non-irritating as well as strong enough to hold the tubing in place. The wrap stays away from the site of surgery by its special shape and configuration and use of adjustable straps 177, 178, 179, 180, 181. These straps connect to each other with use of snaps as well as adhesive surfaces. The end part of these straps have an area of adhesive covered by a plastic cover that is removed to expose the adhesive surface that will adhere to the appropriate surface of the strap. This end will go through a bridge or snap on the other matching end to make a U-turn similar to one shown in FIG. 2, and then to stick to its own back and make a sturdy attachment. Other commonly used small snaps may also be used to adjust its length. After the wrap is in proper place, then tubing 182 comes to be situated inside a canal 172 in tray 171. The draining tube will be held in place with use of a flap 175 (only part of this flap is shown here). The tip of the end of this flap goes through a bridge 176 to be fixed as in FIGS. 1 and 2. The draining tubing 182 continues then to join a plastic bladder 183 shown here in dotted line. This bladder is held in a pocket 173 which is located on the wrap. This pocket holds the bladder 183 securely in place with use of an elastic edge 174 shown here as a zig-zag line. As I mentioned earlier, the length of the straps can be adjusted easily by using snaps. In some models, the rear surface of the wrap may also have an adhesive surface covered with plastic that is used to help in keeping it in place securely.

A similar wrap for use after certain operations in the chest such as breast operations, etc., is shown in FIG. 40.

What is claimed is:

1. A wrapping unit for holding an invasive device externally on the body comprising a wrap for encircling a portion of the body, said wrap including a support member comprising cradle means facing away from the encircled portion of the body for receiving an external portion of such an invasive device, said wrap including a flap having one end portion thereof attached to said wrap adjacent a first side of said cradle means, bridge means disposed on said wrap adjacent a second side of said cradle means that lies opposite said first side, said flap extending from said one end portion thereof in overlying relation to said cradle means to pass through said bridge means for holding such an invasive device in said cradle means, said flap making a U-turn after passing through said bridge means, and said flap extending from such U-turn over said bridge means to another end portion of said flap, and means releasably securing said another end portion of said flap to said flap at a location that is between said bridge means and the attachment of said one end portion of said flap to said wrap.

2. A wrapping unit as set forth in claim 1 in which said bridge means is disposed on said support member.

3. A wrapping unit as set forth in claim 1 in which said location overlies said cradle means.

4. A wrapping unit as set forth in claim 3 further including a transparent pocket disposed on said flap between said location and the attachment of said one end portion of said flap to said wrap for holding sheet material containing information relating to use of the wrapping unit.

5. A wrapping unit as set forth in claim 4 further including a second transparent pocket disposed on said wrap proximate said first transparent pocket but beyond the attachment of said one end portion of said flap to said wrap.

6. A wrapping unit as set forth in claim 1 in which said cradle means comprises means defining a canal that begins at an edge portion of said support member, extends in a loop that passes beneath itself, and ends at said edge portion.

7. A wrapping unit as set forth in claim 6 in which said edge portion of said support member comprises parallel edge segments, the beginning of said canal is at one of said edge segments, and the end of said canal is a another of said edge segments.

8. A wrapping unit as set forth in claim 1 in which said support member comprises a first part and a second part that is separably mounted on said first part, and said cradle means is in said second part.

9. A wrapping unit as set forth in claim 8 in which said second part is selectively positionable on said first part.

10. A wrapping unit as set forth in claim 9 in which said first and second parts have serrated edges that are fitted to each other.

11. A wrapping unit as set forth in claim 8 in which said second part separably mounts on said first part by sliding engagement with said first part.

12. A wrapping unit as set forth in claim 8 in which a second cradle means is provided on said first part for holding a second invasive device between said first cradle means and one of said bridge means and the attachment of said flap to said wrap so that said flap overlies both cradle means as it extends from its attachment to said wrap to said bridge means.

13. A wrapping unit as set forth in claim 1 further including an elastic rimmed pocket disposed on said wrap for holding a bladder of such an invasive device.

14. A wrapping unit for holding first and second invasive devices externally on the body comprising a wrap for encircling a portion of the body, said wrap including a support member comprising first and second cradle means facing away from the encircled portion of the body for receiving external portions of such invasive devices, and means for releasably holding such external portions of such devices in said first and second cradle means, and wherein one of said cradle means is selectively laterally positionable on said support member relative to the other of said cradle means to provide a desired lateral spacing between such devices.

15. A wrapping unit as set forth in claim 14 wherein said support member comprises a plastic base part that contains said first cradle means as a formed pocket in said plastic base part, and another plastic part that contains said second cradle means as a formed pocket in said another plastic part, wherein said another plastic part is selectively laterally positionable on said plastic base part.

16. A wrapping unit for holding an invasive device externally of the body comprising a wrap for encircling a portion of the body proximate an invasion site, said wrap comprising support means for supporting such a device, said support means comprising a first part attached to said wrap and a second part separably mounted on said first part, wherein said second part comprises cradle means for receiving an external portion of such a device, and means for releaseably holding such external portion of such a device in said cradle means.

17. A wrapping unit as set forth in claim 16 in which said second part separably mounts on said first part by means of a sliding connection whereby said second part slides onto said first part.

18. A wrapping unit as set forth in claim 16 in which said second part separably mounts on said first part by means of adhesive.

19. A wrapping unit as set forth in claim 16 in which said second part separably mounts on said first part by means of a Velcro (tm) patch on said second part that sticks to a Velcro (tm) patch on said first part.

20. A wrapping unit as set forth in claim 16 in which said second part separably mounts on said first part by means of a flap extending from said wrap.

21. A wrapping unit as set forth in claim 16 wherein said first part is a plastic part, said second part is a plastic part that contains said cradle means as a formed pocket therein, and wherein said second plastic part is selectively laterally positionable on said first part.

22. A wrapping unit as set forth in claim 21 wherein said first part contains a further cradle means formed as a pocket therein and also a formed slot leading to a location where said second part is disposed on said first part, and wherein said second part contains its own formed slot extending from the cradle means thereof to said formed slot of said first part.

* * * * *